US00PP29275P3

(12) United States Plant Patent
Layt

(10) Patent No.: US PP29,275 P3
(45) Date of Patent: May 8, 2018

(54) ***EREMOPHILA* PLANT NAMED 'EREM1'**

(50) Latin Name: *Eremophila glabra*
Varietal Denomination: EREM1

(71) Applicant: Todd Anthony Layt, Clarendon (AU)

(72) Inventor: Todd Anthony Layt, Clarendon (AU)

( * ) Notice: Subject to any disclaimer, the term of this patent is extended or adjusted under 35 U.S.C. 154(b) by 45 days.

(21) Appl. No.: 14/999,684

(22) Filed: Jun. 14, 2016

(65) Prior Publication Data

US 2017/0359931 P1 Dec. 14, 2017

(30) Foreign Application Priority Data

Jun. 15, 2015 (AU) ..... PBR 2015146

(51) Int. Cl.
*A01H 5/02* (2018.01)
*A01H 5/12* (2018.01)

(52) U.S. Cl.
USPC ..... Plt./226
CPC ..... *A01H 5/02* (2013.01); *A01H 5/12* (2013.01)

(58) Field of Classification Search
None
See application file for complete search history.

(56) References Cited

PUBLICATIONS

UPOV hit on *Eremophila* plant named 'Erem1', AU PBR 2015146, filed Jun. 15, 2015.*

* cited by examiner

*Primary Examiner* — Anne Marie Grunberg
(74) *Attorney, Agent, or Firm* — Samuel R. McCoy, Jr.

(57) ABSTRACT

A new and distinct *Eremophila glabra* cultivar named 'EREM1' which is characterized by a prostrate growth habit with a vigorous growth rate, silver ovate foliage, and the stability of these characteristics from generation to generation.

3 Drawing Sheets

Latin name of the genus and species: The Latin name of the genus and species of the novel variety disclosed herein is *Eremophila glabra*.

Variety denomination: The inventive variety of *Eremophila glabra* disclosed herein has been given the variety denomination 'EREM1'.

CROSS REFERENCE TO RELATED APPLICATIONS

This application claims priority to the Australian Plant Breeder's Rights application number 2015/146, filed on Jun. 15 2015, which is herein incorporated by reference.

BACKGROUND OF THE INVENTION

Parentage: 'EREM1' is a naturally-occurring whole plant mutation of a low-growing *Eremophila glabra* plant (unnamed and unpatented) which was discovered in September of 2013 by the inventor at his commercial nursery in Clarendon, New South Wales, Australia. In 2012, the parent plant was asexually reproduced by way of stem cuttings. Of the resulting plants, one plant in particular exhibited improved plant vigor and a prostrate growth habit. The new plant was isolated and grown to a mature size to confirm the distinctness and stability of the characteristics initially observed. After further evaluation and confirmation of the desirable traits, the claimed plant was selected for commercialization and given the breeder denomination, 'EREM1'.

Asexual Reproduction: 'EREM1' was first asexually reproduced by way of softwood stem cuttings in 2013 at the inventor's nursery in Clarendon, New South Wales, Australia. It was found to grow uniform and reproduce in a stable manner and 5 successive cycles of vegetative propagation have proven to be true to type also.

SUMMARY OF THE INVENTION

The following characteristics have been repeatedly observed and represent the distinguishing characteristics of the new *Eremophila* cultivar 'EREM1'. These traits, in combination, distinguish 'EREM1' as a new and distinct cultivar.

1. 'EREM1' exhibits a short plant height and prostrate growth habit; and
2. 'EREM1' exhibits a very vigorous rate of growth; and
3. 'EREM1' exhibits foliage with a silver appearance; and
4. 'EREM1' exhibits obovate foliage.

BOTANICAL DESCRIPTION OF THE PLANT

Figure 1:
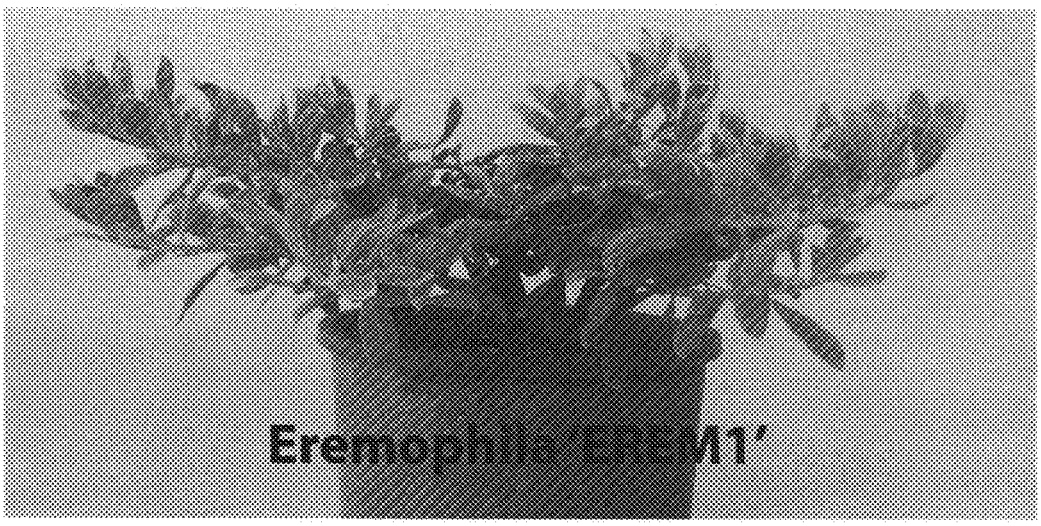
FIG. 1 illustrates, as nearly true as it is reasonably possible to make the same in color photographs of this type, an exemplary 1 year old 'EREM1' plant grown outdoors in Clarendon, New South Wales, Australia.
Figure 2:
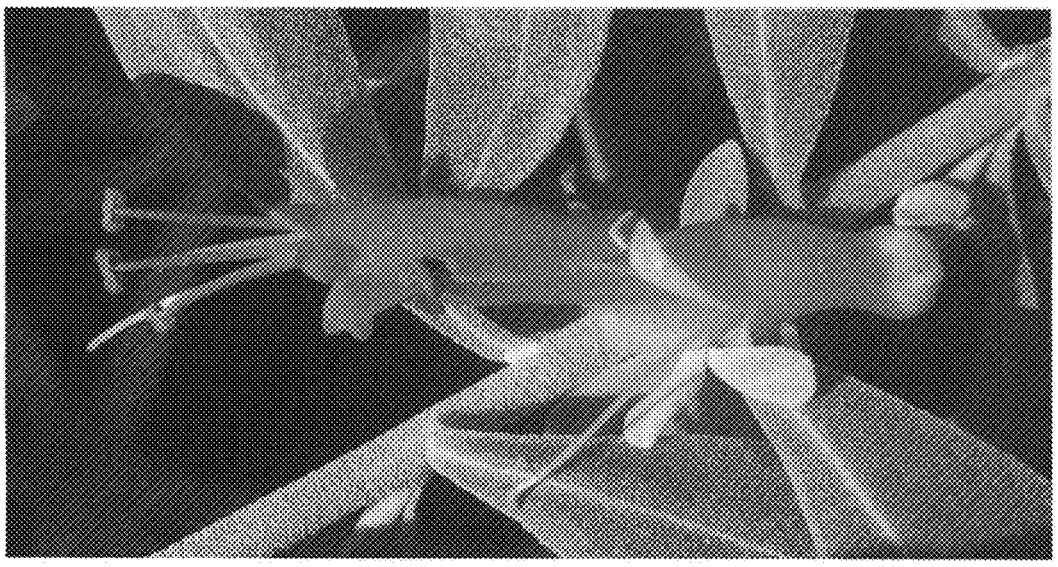
FIG. 2 illustrates, as nearly true as it is reasonably possible to make the same in color photographs of this type, an exemplary flower of a 1 year old 'EREM1' plant grown outdoors in Clarendon, New South Wales, Australia.
Figure 3:
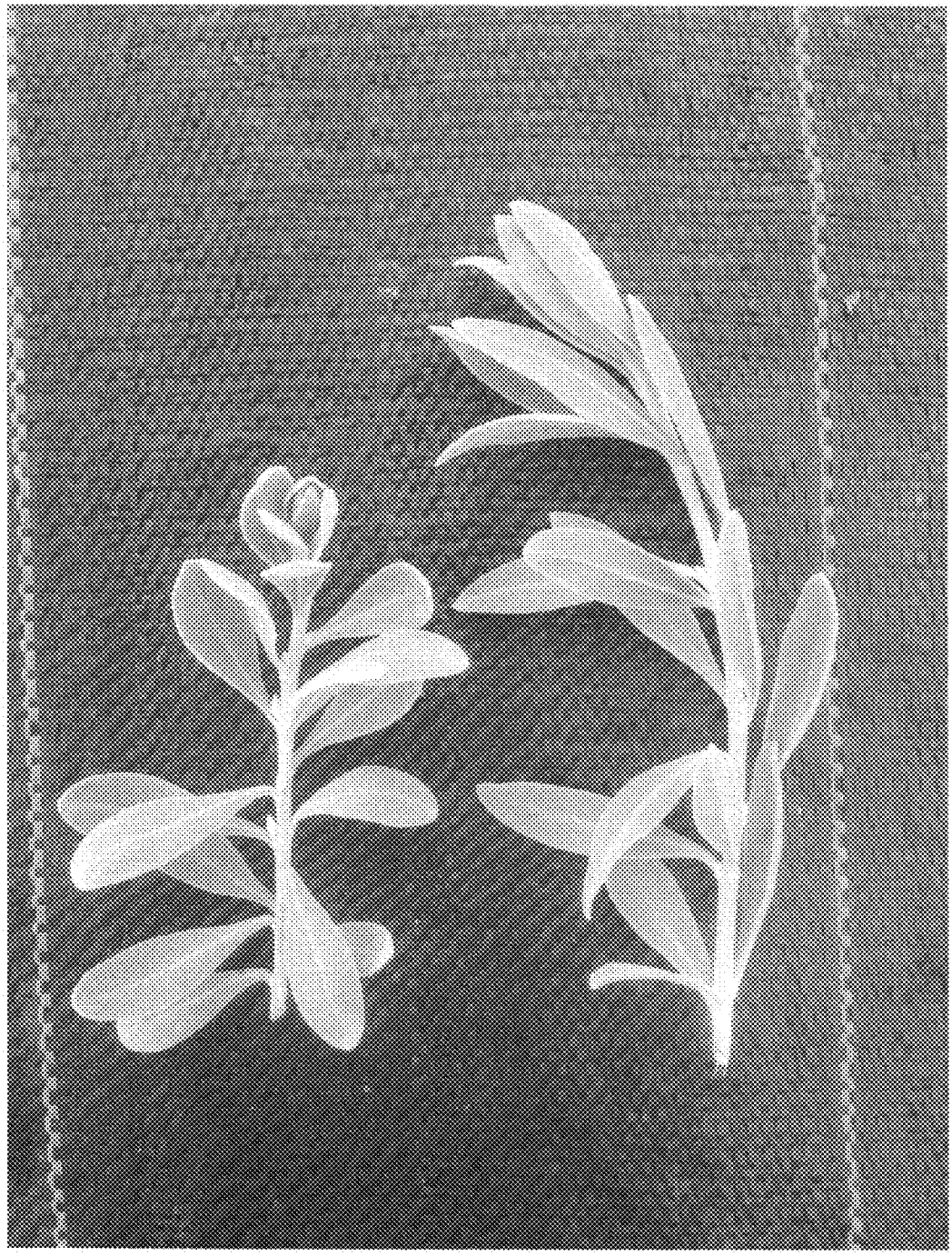
FIG. 3 illustrates, as nearly true as it is reasonably possible to make the same in color photographs of this type, a stem and foliage comparison between a 1 year old 'EREM1' plant, on the left, and a 'Kalbarri Carpet' (unpatented) plant of similar age, both grown outdoors in Clarendon, New South Wales, Australia.

The following is a detailed botanical description of a new and distinct variety of a *Eremophila* ornamental plant known as 'EREM1'. Plant observations were made on plants grown in Clarendon, New South Wales, Australia. Unless indicated otherwise, the descriptions disclosed herein are based upon observations made from 1 year old mature 'EREM1' plants grown outdoors in full sun. Plants were fertilized with a slow release granular fertilizer product and were periodically watered with overhead irrigation, as needed. No pest and disease measures were taken. Observation data was recorded in the June of 2016.

Those skilled in the art will appreciate that certain characteristics will vary with older or, conversely, younger plants. 'EREM1' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart,* The Royal Horticultural Society, London, 2001 edition except where common terms of color are used.

A botanical description of 'EREM1' and comparisons with the presumed parents are provided below.

General plant description:

*Plant habit.*—Prostrate; spreading.

*Height.*—Approximately 200 to 250 mm.

*Width.*—Approximately 700 mm.

*Hardiness.*—USDA Zone 9.

*Environmental tolerances.*—'EREM1' has not yet been observed under all conditions but has shown to be heat tolerant, adapting well to temperatures of 112 degrees Fahrenheit without any noticeable damage. It has survived light frosts and temperatures down to 23 degrees Fahrenheit.

*Drought tolerance.*—'EREM1' has not yet been observed under all conditions but it has shown good drought tolerance typical of the species once established.

*Pest and disease susceptibility or resistance.*—No known pests.

*Propagation.*—Propagation is accomplished using softwood stem cuttings.

*Time to develop roots.*—4 to 5 weeks.

*Crop time.*—From 8 to 10 weeks are needed to produce a fully rooted cutting and 30 weeks to produce a marketable plant in a 140 mm nursery pot, depending on geographic location.

Root system:

*Description.*—Dicotyledonous with a tap root system. From cuttings the roots are adventitious with one or two becoming somewhat like a true tap root in function. Roots are white, smooth and branching.

Stems:

*Branching habit.*—Trunk — Single main trunk branching numerous times above the ground. Diameter — To approximately 15 mm. Color — Light brown (no corresponding R.H.S. color). Texture — Minor fissures. Secondary stems — Stem strength — Medium. Diameter — Intermediate stems to 8 mm; young stems 2 to 4 mm. Cross-section — Circular. Internode length — 3 mm. Number of stems — 17. Stem angle to main axis — Approximately 45 degrees. Basal stem color (hair removed) — RHS N144C. Young shoot stem color (hair removed) — RHS N144C. Texture — Densely pubescent.

Foliage:

*Arrangement.*—Alternate.

*Attachment.*—Sessile.

*Division.*—Simple.

*Shape.*—Obovate to elliptical.

*Length.*—Approximately 45 mm.

*Width.*—15 mm.

*Thickness.*—0.5 mm.

*Apex.*—Acute.

*Base.*—Cuneate.

*Margin.*—Entire.

*Texture and pubescence, adaxial surface.*—Finely and densely pubescent.

*Texture and pubescence, abaxial surface.*—Finely and densely pubescent.

*Color.*—Juvenile foliage, adaxial surface — RHS 191A. Juvenile foliage, abaxial surface — RHS 191A. Mature foliage, adaxial surface — RHS 189A. Mature foliage, abaxial surface — RHS 189A.

*Venation.*—Pattern — Only the main vein is visible. Vein color, adaxial surface — RHS 190B. Vein color, abaxial surface — RHS 190B.

*Petiole.*—None; leaves sessile.

Inflorescence:

*Type.*—Solitary flowers occurring at the leaf axils.

Bud:

*Dimensions.*—Approximately 15 mm long and 8 mm in diameter.

*Shape.*—Blunt, pointed tube extending from the calyx as it matures.

*Color, upper surface.*—RHS 165B.

*Color, lower surface.*—RHS 153A.

*Rate of opening.*—Slow to medium.

Flower:

*General description.*—Zygomorphic, tubular flower comprised of a corolla tube and four dorsal petal lobes and one longer ventral lobe. Solitary flowers occurring within the foliage.

*Natural flowering season.*—Early winter in Clarendon, New South Wales, Australia.

*Bloom habit.*—Moderately floriferous.

*Abundance of flowers.*—Very abundant.

*Lastingness.*—5 days.

*Persistence.*—Not persistent.

*Fragrance.*—Not fragrant.

*Aspect.*—Horizontal.

*Pedicels.*—Attitude, relative to stems — Semi-erect; approximately 45 degrees. Dimensions — 3 to 5 mm long and 1 mm wide. Color — RHS 191A. Texture and pubescence — Finely and densely pubescent. Strength — Strong.

*Calyx.*—Quantity of sepals — 5 fused tepals. Arrangement — Fused into a lobed tube. Dimensions — 5 mm wide and 8 mm long, including the sepal lobes. Sepal lobe apex — Acute. Sepal lobe margin — Entire; finely and densely pubescent. Texture, inner and outer surfaces — Finely and densely pubescent.

Color when opening, inner surface — RHS 191A. Color when opening, outer surface — RHS 191A. Color when fully open, inner surface — RHS 191A. Color when fully open, outer surface — RHS 191A.

*Corolla.*—Quantity of petals — Five. Arrangement — Fused into a curved tube with five free lobes: four dorsal lobes and one ventral lobe transformed into a lip. Dorsal lobes are approximately 4 mm long and the ventral lip is 10 mm. Dimensions — 22 mm long and 10 mm in diameter. Petal lobe apex — Acute. Petal lobe margin — Entire. Texture, inner and outer surfaces — Finely and densely pubescent. Color when opening, inner surface — RHS 20A. Color when opening, outer surface — RHS 20A. Color when fully open, dorsal surface — 31A. Color when fully open, ventral surface — 20A. Petal color fading to — RHS 31A.

Reproductive organs:

*Stamens.*—Quantity — Four. Position — Exserted; at anthesis, the stamens exceed the length of the corolla. Overall length — 30 mm long. Filament — Dimensions — 30 mm long and 0.5 mm in diameter. Color — RHS 20A. Anthers — Shape — Round and flattened. Diameter — 1 mm in diameter and 0.25 mm thick. Color — RHS 177A. Pollen — Low to medium. Pollen Color — White (no corresponding R.H.S. color).

*Pistils.*—Quantity — One pistil which extends beyond the corolla at anthesis. Stigma — Shape — Globular. Dimensions — Less than 1 mm in diameter. Color — Yellow (no corresponding R.H.S. color). Style — Shape — Slightly curved towards the distal end. Dimensions — 40 mm long and less than 1 mm wide. Color — RHS 18C. Ovary — Position — Superior. Dimensions — 1.5 mm long and 1.5 mm wide. Color — 20A.

Fruit and seed:

*Fruit.*—Type — Semi-succulent. Shape — Ovoid. Dimensions — Approximately 8 mm in diameter. Texture — Smooth to finely and sparsely hairy. Color — RHS 166D at maturity.

*Seed.*—Quantity — Usually two per fruit. Shape — Flattened ovoid with a slightly textured surface. Dimensions — 3 mm long and 1 mm in diameter. Color — RHS 163C.

Comparison with the parent: 'EREM1' may be distinguished from the parent, a low-growing *Eremophila glabra* plant (unnamed and unpatented), by the general plant height and plant vigor. Plants of 'EREM1' are very vigorous and exhibit a very short plant height, whereas the parent plant exhibits a medium to tall plant height and are less vigorous.

Comparisons with the closest known variety: 'EREM1' may be distinguished from its closest know commercial comparator, *Eremophila glabra* 'Kalbarri Carpet' (unpatented) by the following combination of characteristics: 1. EREM1' grows to approximately 200 to 250 mm tall, whereas 'Kalbarri Carpet' grows to approximately 150 mm tall. 2. The leaves of 'EREM1' are of short to medium length with an obovate shape, whereas leaves of 'Kalbarri Carpet' are of medium to long length and lanceolate. 3. The stem internodes of 'EREM1' are shorter than those of 'Kalbarri Carpet.

That which is claimed is:

1. A new and distinct variety of *Eremophila glabra* plant named 'EREM1', substantially as described and illustrated herein.

* * * * *